United States Patent
Jones

(10) Patent No.: US 6,681,590 B1
(45) Date of Patent: Jan. 27, 2004

(54) HEAD COOLING COMPRESS WITH REMOVABLE, SELF CLOSING FABRIC COVER

(75) Inventor: Barbara Ann Jones, San Diego, CA (US)

(73) Assignees: Barbara A. Jones; Jeffrey R. Jones, San Diego, CA (US)

( * ) Notice: Subject to any disclaimer, the term of this patent is extended or adjusted under 35 U.S.C. 154(b) by 0 days.

(21) Appl. No.: 10/405,219

(22) Filed: Apr. 3, 2003

(51) Int. Cl.[7] ............................................... F25D 23/12
(52) U.S. Cl. ......................................... 62/259.3; 62/530
(58) Field of Search ................................. 62/259.3, 530, 62/457.2, 457.3

(56) References Cited

U.S. PATENT DOCUMENTS

| | | | | |
|---|---|---|---|---|
| 4,744,106 A | * | 5/1988 | Wang | 2/171.3 |
| 5,146,765 A | * | 9/1992 | Waters | 62/259.3 |
| 5,197,292 A | * | 3/1993 | McPherson | 62/56 |
| 5,327,585 A | * | 7/1994 | Karlan | 2/7 |
| 5,715,533 A | * | 2/1998 | Stein | 2/7 |
| 6,125,636 A | * | 10/2000 | Taylor et al. | 62/3.5 |
| 6,189,327 B1 | * | 2/2001 | Strauss et al. | 62/259.3 |
| 6,438,964 B1 | * | 8/2002 | Giblin | 62/3.5 |
| 6,543,247 B2 | * | 4/2003 | Strauss | 62/259.3 |

* cited by examiner

*Primary Examiner*—Melvin Jones

(57) ABSTRACT

The invention is a head cooling compress, positioned for the top of a human head, generally used under a cap or hat. The device consists of a reusable, refreezable, 4"×4" gel cold pack enclosed in a removable, washable, self closing fabric bag. The hermetically sealed gel pack will remain flexible when frozen to a low temperature of 20 degrees farenheit. The 4.5"×4.5" fabric bag consists of a washable terry/velour fabric with a self closing feature which will allow the gel pack to be removed. The self closing feature consists of overlapping fabric similar to the back of a pillow sham. A further purpose of this device is because of it's small size and shape to be used as a covered therapeutic cold pack for bodily afflictions, injuries, and trauma. A VELCRO hook style fastener with a semi-permanent adhesive backing will secure said fabric bag to the inside top of a cap or hat.

3 Claims, 1 Drawing Sheet

HEAD COOLING COMPRESS WITH REMOVABLE, SELF CLOSING FABRIC COVER

CROSS-REFERENCE TO RELATED APPLICATIONS

U. S. Patent Documents

| | | | | |
|---|---|---|---|---|
| 1567931 | Dec., | 1925 | Epler | 150/2 |
| 1964962 | Jul., | 1934 | Rosenblum | 150/2 |
| 2984839 | May., | 1961 | Conrad et al. | 2/7 |
| 3149943 | Sep., | 1964 | Amador | 128/402 |
| 3175558 | Mar., | 1065 | Caillouette et al. | 128/403 |
| 3463161 | Aug., | 1969 | Andrassy | 128/402 |
| 3506013 | Apr., | 1970 | Zdenek | 128/402 |
| 3623485 | Nov., | 1971 | Price | 128/402 |
| 3696814 | Oct., | 1972 | Umemoto | 128/402 |
| 3717145 | Feb., | 1973 | Berndt et al. | 128/82 |
| 3830676 | Aug., | 1974 | Elkins | 128/403 |
| 3889684 | Jun., | 1975 | Lebold | 128/402 |
| 3900035 | Aug., | 1975 | Welch et al. | 128/402 |
| 3943988 | Mar., | 1976 | Consorti | 150/7 |
| 3950789 | Apr., | 1976 | Konz et al. | 128/402 |
| 4044773 | Aug., | 1977 | Baldwin | 128/402 |
| 4055188 | Oct., | 1977 | Pelton | 128/402 |
| 4081150 | Mar., | 1978 | Tyson | 128/402 |
| 4092982 | Jun., | 1978 | Salem | 128/402 |
| 4108351 | Aug., | 1978 | Hough | 150/7 |
| 4114620 | Sep., | 1978 | Moore et al. | 128/254 |
| 4190054 | Feb., | 1980 | Brennan | 128/402 |
| 4204543 | May, | 1980 | Henderson | 607/112 |
| 4381025 | Dec., | 1981 | Schooley | 607/112 |
| 4324111 | Apr., | 1982 | Edwards | 62/530 |
| 4326533 | Apr., | 1982 | Henderson | 607/112 |
| 4354496 | Oct., | 1982 | Andersen | 128/339 |
| 4356709 | Nov., | 1982 | Alexander | 62/530 |
| 4552149 | Mar., | 1983 | Tatsuki | 607/110 |
| 5197292 | Mar., | 1983 | McPherson | 2/7 |
| 4382446 | May., | 1983 | Trvelock et al. | 128/403 |
| 4381025 | Apr., | 1983 | Schooley | 150/2 |
| 4404820 | Sep., | 1983 | Romaine | 62/530 |
| 4425916 | Jan., | 1984 | Brown | 128/402 |
| 4425917 | Jan., | 1984 | Kuznetz | 128/399 |
| 4551858 | Nov., | 1985 | Pasternack | 2/7 |
| 4815144 | Jun., | 1987 | Martin | 2/7 |
| 4941210 | Dec., | 1988 | Konucik | 2/171 |
| 4910978 | Feb., | 1989 | Gordon | 62/530 |
| 5054122 | Oct., | 1991 | Sher | 2/7 |
| 5469579 | Jan., | 1994 | Tremblay | 2/7 |

BACKGROUND OF THE INVENTION

Last summer, my son became overheated during an outdoor basketball game and could not continue playing. Before the next game, I repackaged liquid from a standard size gel pack bag into a smaller size bag and devised a small cloth pouch to hold it. At the game, when he started to get too hot, I placed the bag with the now frozen gel pack under his cap. Within a few minutes, I noticed an improvement in his actions, energy and overall appearance. Many of the other parents observed this phenomenon and asked me to make the same for their children as well.

Many sports and other activities take place in high temperature environments which can be uncomfortable for participants and spectators. In addition, many strenuous activities in high temperature environments often subject humans to extreme heat and the accompanying fatigue and discomfort.

Head cooling devices having compartments containing ice are not new As stated in U.S. Pat. No. 5,469,579 issued to Tremblay. In this patent, Mr. Tremblay has enclosed a pocket for ice cubes held in a safety helmet by means of flexible bands. The result of this device would allow water droplets from the melting ice cubes to drip freely onto the person's head. Anyone wanting to cool their head using this product,would need to wear a helmet and have a wet head. This is very impractical for most people.

Another example of a head cooling device is stated in U.S. Pat. No. 4,522,149 issued to Tatsuki. Mr. Tatsuki uses a whole head unit in the form of a cap having a chin strap or fastener-equipped belt to lock the device around the skull. This type of head cooling can only be used in a hospital or behind closed doors. Not very useful for everyday life.

Other types of devices that cool the head or other parts of the body have elastic bands or straps with adjustable devices. U.S. Pat. No. 4,326,533 issued to Henderson is an example of strapping a cooling device by means of elastic bands to ones body. Ms. Henderson's device encircles the human head making it difficult to slide a hat or other head gear on the head. The "ones-size-fits-all" approach to an elastic band around the head is impractical. The elastic bands would also hold in heat causing the head to sweat and compromising the units ability to cool.

My device overcomes these mentioned disadvantages associated with devices of the prior art by providing a device which can be worn under any existing hat or cap. A device that is an individual gel bag that can be reused and is flexible when frozen, contained in a removable, washable terry/velour cloth bag. The cover will also absorb perspiration and any condensation from the frozen gel bag, thus keeping the head dry, cool, and comfortable.

A purpose of this new and improved coolant device with its small size being more convenient, easier to use, and very mobile.

It is also the purpose of this invention to provide a removable terry/velour bag to hold said coolant device.

It is also the purpose of this invention to provide a self closing feature of the terry/velour bag which will hold the gel pack secure in the bag as to prevent slippage or the gel pack from falling out. The self closing feature allows the gel pack to be secure in the fabric bag without the addition of hooks, buttons, snaps or other such closing mechanisms which would take away from the comfort.

It is also the purpose of this invention to provide a, refreezable, reusable, non-toxic liquid gel coolant, hermetically sealed in a polybag, to be enclosed in the terry/velour bag.

It is yet another purpose of this invention to provide a "coin" type fastener commonly marketed under the trade name of VELCRO to be able to attach said invention sto the inside of any cap or hat of ones choosing by means of the semi-permanent adhesive on the back of the fastener.

It is still a further purpose to provide a coolant device which will remain flexible when frozen and which can be quickly and easily removed from a freezer or portable insulated cooler and inserted into the provided terry/velour fabric bag.

A further purpose of this device is because of it's small size and shape to be used as a covered therapeutic cold pack for bodily afflictions, injuries, and traumas.

BRIEF SUMMARY OF THE INVENTION

The general idea of the invention is to give cool relief to a human being while engaged in activities during high temperature environments.

The advantage of this invention is the shape and small size, only 4.5"×4.5". It will fit under most caps or hats without a misshapen outline or causing a cap/hat to not fit well. The terry/velour fabric pocket cover, is designed with a self closing feature to hold the coolant device. The coolant device is a non-toxic gel, hermetically sealed in a 4+ mil poly bag. The gel will remain flexible when frozen to better conform to a head or other parts of a body. Once frozen and inserted into the terry/velour bag, the gel cold pack will give cool comfort to a human head. The terry/velour bag will absorb excess moisture from sweat or the condensation of the cold pack itself, adding to the comfort of the piece. The gel cold pack can be easily removed to wash the outer terry/velour bag. Attached to the terry side of the cover is a removable VELCRO "coin". The "coin" hooks into the terry side of the pack while it's adhesive backing will hold the pack in place against the inside top of a cap or hat keeping the fabric covered gel pack from slipping.

BRIEF DESCRIPTION OF THE DRAWINGS

In the accompanying drawings;

Referring in detail to the drawing, FIG. 1 illustrates a typical brim cap, also known as a baseball cap A showing the placement of the VELCRO "coin" B with adhesive backing C into said cap to prepare for the insertion of FIG. 2 the bag containing the gel cold pack.

Referring to FIG. 2 the 4.5" by 4.5" fabric bag with enclosed 4" by 4" gel pack. The gel pack E, is shown inside the large pocket opening of the fabric bag F and tucked in using D, the 1" of overlapping extra fabric to secure gel pack into pouch. This overlapping of fabric is the same method used to tuck a pillow into a pillow sham. This self closing feature allows the bag to secure in the gel pack within the fabric bag without the addition of hooks, buttons, snaps or other such closing mechanisms. FIG. 2 also shows the sewn seam H of velour fabric G with loop terry fabric F. The fabric is sewn on three sides with a finished edge on the opened side of the terry fabric. It is the looped terry fabric which will be hooked into the VELCRO coin B in FIG. 1.

Referring to FIG. 3 the cut-away view. This illustrates how the extra 1" of the velour fabric D with finished edge, will be folded back onto itself and sewn using the same seams of F/G. The overlapping of D and F will form the closure necessary to hold in the gel pack without having to use mechanical devices.

DETAILED DESCRIPTION OF THE INVENTION

Figure 1:
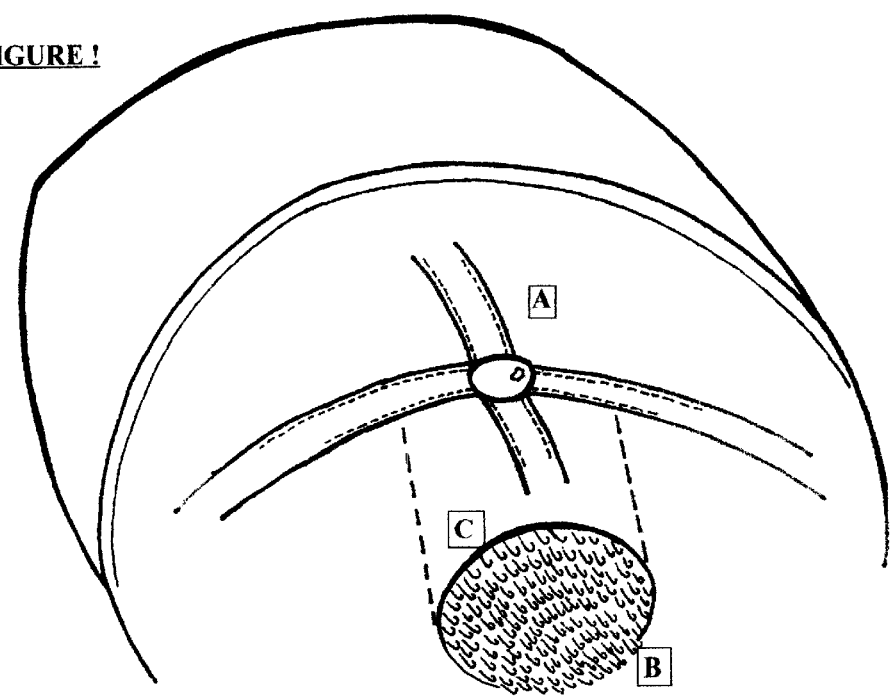
FIG. 1 depicts the inside top of cap.
Figure 2:
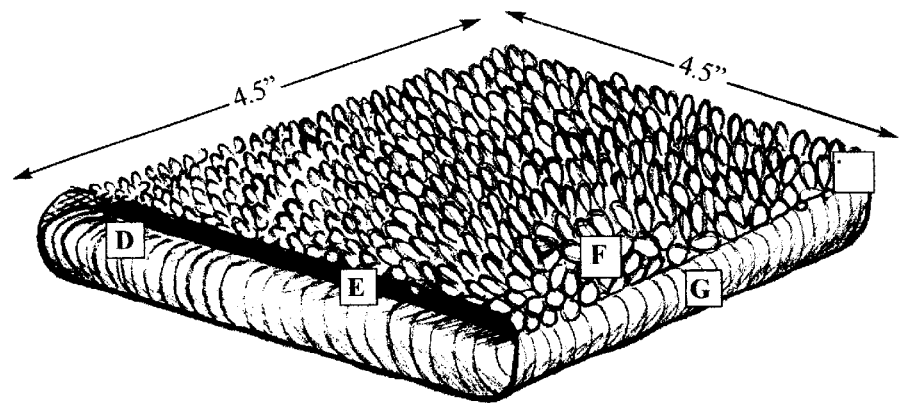
FIG. 2 shows the fabric bag with enclosed gel cold pack.
Figure 3:
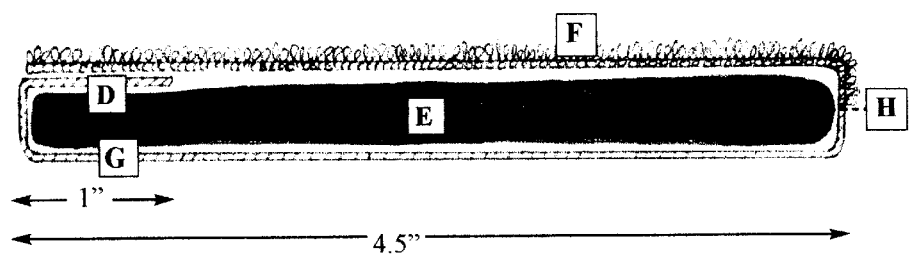
FIG. 3 is a cut-away view of the fabric bag with enclosed gel cold pack.

The invention consists of a 4"×4" re-usable, re-freezable, gel cold pack filled with a non-toxic liquid which when frozen will remain flexible.

The gel pack will be enclosed by a cloth bag made up of a velour-terry fabric. One side of the bag is velour fabric and the other side of the bag is a terry fabric. The fabric will be cut and sewn to fit the 4"×4" gel pack with allowable room for seams. The fabric will be stitched together in the shape of a bag, using a "surger' stitching method. This method will bind the seams together to make sure the seams do not fray. (start to unravel). One side of the pouch will be an opening to tuck the gel pack into the pocket The gel pack will then be back tucked into the small 1" of overlapping fabric to secure said gel pack into the bag. This self closing method will allow the gel pack to tuck within the main pouch similar to the tucking of a pillow in a fitted pillow sham. This self closing feature will keep the contents of the bag from falling out. The velour side will be worn against the human head, while the terry side, which has loops, will be hooked into a circular "velcro" type "coin". The "coin" is approximately 1.5" to 2" circular with a semi permanent adhesive on one side and hook like barbs on the other. The adhesive backing of the "coin" will allow for securing the bag with the inserted gel pack to the top of the inside of a cap or hat to prevent slippage.

I claim:

1. A small 4.5"×4.5" cooling compress comprising;

(a) a non-toxic, refreezable liquid or semi-liquid enclosed and hermetically sealed in a polybag, (b) a non-toxic, refreezable liquid or semi-liquid enclosed and sealed in a polybag to remain flexible to a low temperature of about 20 degrees fahrenheit, (c) a terry/velour fabric bag to contain said cooling compress which has an overlapping, self closing feature to insure retention of said compress without the use of closing mechanisms, (d) a terry fabric bag with overlapping fabric opening for insertion and removal of said coolant compress, (e) a terry fabric bag capable of absorbing perspiration and absorbing condensation from the frozen bag, and which can be washed when necessary.

2. A small cooling compress as set forth in claim 1 wherein said outwardly surface has a removable VELCRO "coin" with semi-permanent adhesive backing to secure said bag to the inside top of hats, helmets, caps or other headgear and the like.

3. A small cooling compress as set forth in claim 1 enclosed with in the terry/velour fabric bag to be used as a covered therapeutic cold pack for bodily afflictions, injuries, and traumas.

* * * * *